US012564381B2

(12) United States Patent
Wang et al.

(10) Patent No.: US 12,564,381 B2
(45) Date of Patent: Mar. 3, 2026

(54) SYSTEMS AND METHODS FOR CONTRAST ENHANCED IMAGING

(71) Applicant: KONINKLIJKE PHILIPS N.V., Eindhoven (NL)

(72) Inventors: Shiying Wang, Melrose, MA (US); Thanasis Loupas, Bothell, WA (US); Jeffry Earl Powers, Bainbridge Island, WA (US); Claudia Errico, Cambridge, MA (US); William Tao Shi, Wakefield, MA (US); Paul Sheeran, Woodinville, WA (US); Charles Tremblay-Darveau, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 506 days.

(21) Appl. No.: 17/417,137

(22) PCT Filed: Dec. 23, 2019

(86) PCT No.: PCT/EP2019/086894
§ 371 (c)(1),
(2) Date: Jun. 22, 2021

(87) PCT Pub. No.: WO2020/141127
PCT Pub. Date: Jul. 9, 2020

(65) Prior Publication Data
US 2022/0071596 A1 Mar. 10, 2022

Related U.S. Application Data

(60) Provisional application No. 62/880,107, filed on Jul. 30, 2019, provisional application No. 62/787,860, filed on Jan. 3, 2019.

(51) Int. Cl.
*A61B 8/00* (2006.01)
*G06T 5/50* (2006.01)
(Continued)

(52) U.S. Cl.
CPC .............. *A61B 8/481* (2013.01); *A61B 8/467* (2013.01); *A61B 8/5207* (2013.01);
(Continued)

(58) Field of Classification Search
CPC ....... A61B 8/481; A61B 8/467; A61B 8/5207; A61B 8/5246; A61B 8/5276; A61B 8/085;
(Continued)

(56) References Cited

U.S. PATENT DOCUMENTS 6,368,277 B1 * 4/2002 Mao ......................... A61B 8/08
600/441
6,443,896 B1 9/2002 Detmer
(Continued)

FOREIGN PATENT DOCUMENTS

JP 2018015155 A * 2/2018
WO WO-2009130647 A1 * 10/2009 ............. A61B 8/463
(Continued)

OTHER PUBLICATIONS

"Ultrafast ultrasound localization microscopy for deep super-resolution vascular imaging", Nature, vol. 527, No. 7579, Nov. 26, 2015 (Nov. 26, 2015), pp. 499-502, XP055390064, GB ISSN: 0028-0836, DOI (Year: 2015).*
(Continued)

*Primary Examiner* — Pascal M Bui Pho
*Assistant Examiner* — Nicholas A Robinson

(57) ABSTRACT

Systems and methods for visualizing microbubbles for contrast-enhanced imaging are described herein. Microbubbles may be visualized by multi-pixel spots by identifying and localizing individual microbubbles. Motion compensation may be provided for localized microbubbles or for contrast images prior to microbubble identification and localization. Users may determine the size of the multi-pixel spot by
(Continued)

adjusting a filter, for example, adjusting a threshold value of the filter. Altering the size of the multi-pixel spot may alter the resolution. As the number of pixels increases, the resolution decreases, but the acquisition time may also decrease. As the number of pixels decreases, the resolution increases, but the acquisition time may increase.

17 Claims, 7 Drawing Sheets

(51) Int. Cl.
  *G06T 5/92*  (2024.01)
  *G06T 7/20*  (2017.01)
(52) U.S. Cl.
  CPC .......... *A61B 8/5246* (2013.01); *A61B 8/5276* (2013.01); *G06T 5/50* (2013.01); *G06T 5/92* (2024.01); *G06T 7/20* (2013.01); *G06T 2200/24* (2013.01); *G06T 2207/10132* (2013.01); *G06T 2207/20208* (2013.01); *G06T 2207/30101* (2013.01)
(58) Field of Classification Search
  CPC ..... A61B 8/0891; A61B 8/5269; G06T 5/009; G06T 5/50; G06T 7/20; G06T 2200/24; G06T 2207/10132; G06T 2207/20208; G06T 2207/30101
  See application file for complete search history.

(56)            References Cited

U.S. PATENT DOCUMENTS

| | | | |
|---|---|---|---|
| 6,530,885 | B1 | 3/2003 | Entrekin et al. |
| 9,329,260 | B2 | 5/2016 | Couture et al. |
| 2016/0106395 | A1 | 4/2016 | Hynynen et al. |
| 2019/0223828 | A1* | 7/2019 | Torp .................... A61B 8/5207 |
| 2020/0121297 | A1* | 4/2020 | Kim .................... A61B 8/5246 |
| 2020/0178939 | A1* | 6/2020 | Song .................... A61B 8/5223 |
| 2020/0305840 | A1* | 10/2020 | Sboros ..................... G06T 7/73 |
| 2020/0309702 | A1* | 10/2020 | Barron ............... G01N 21/6486 |

FOREIGN PATENT DOCUMENTS

| | | |
|---|---|---|
| WO | 2014179681 A1 | 11/2014 |
| WO | 2017216578 A1 | 12/2017 |
| WO | 2018042191 A1 | 3/2018 |
| WO | 2018134729 A1 | 7/2018 |

OTHER PUBLICATIONS

Song P, Trzasko JD, Manduca A, Huang R, Kadirvel R, Kallmes DF, Chen S. Improved Super-Resolution Ultrasound Microvessel Imaging With Spatiotemporal Nonlocal Means Filtering and Bipartite Graph-Based Microbubble Tracking. IEEE Trans Ultrason Ferroelectr Freq Control. Feb. 2018;65(2) (Year: 2018).*

O'Reilly, M. et al., "Three-Dimensional Transcranial Ultrasound Imaging of Microbubble Clouds Using a Sparse Hemispherical Array", IEEE Transactions on Biomedical Engineering, 2014, vol. 61, No. 4, pp. 1285-1294.

PCT/EP2019/86894 ISR & Written Opinion, Mar. 27, 2020, 15 Page Document.

Christensen-Jeffries et al:"Microbubble Axial Localization Errors in Ultrasound Super-Resolution Imaging"; IEEE Transactions On Ultrasound, vol. 64, Issue 11.

Christensen-Jeffries et al: "In Vivo Acoustic Super-Resolution and Super-Resolved Velocity Mapping Using Microbubbles"; IEEE Trans Med Imaging, 2015, vol. 34(2).

Diamantis et al: "Development of Super-Resolution Sharpness-Based Axial Localization for Ultrasound Imaging"; IEEE, 2018, pp. 6297-6309.

Hansen et al: "Robust Microbubble Tracking for Super Resolution Imaging in Ultrasound"; IEEE International Ultrasonics Symposium Proceedings; 2016, 4 Page Document.

Song et al: "Improved Super-Resolution Ultrasound Microvessel Imaging With Spatiotemporal Nonlocal Means Filtering and Bipartite Graph-Based Microbubble Tracking"; IEEE Tran Ultrason Ferroelectric Frequency Control, Feb. 2018, 65(2), 36 Page Document.

Errico et al: "Ultrafast Ultrasound Localization Microscopy for Deep Super-Resolution Vascular Imaging"; Nature, Nov. 2015, vol. 527, 9 Page Document.

Van Sloun et al: "Super-Resolution Ultrasound Localization Microscopy Through Deep Learning"; IEEE Transactions On Medical Imaging, Mar. 2021, vol. 40(3), pp. 829-839.

* cited by examiner

SYSTEMS AND METHODS FOR CONTRAST ENHANCED IMAGING

CROSS-REFERENCE TO PRIOR APPLICATIONS

This application is the U.S. National Phase application under 35 U.S.C. § 371 of International Application No. PCT/EP2019/086894, filed on Dec. 23, 2019, which claims the benefit of U.S. Provisional Patent Application No. 62/880,107, filed on Jul. 30, 2019 and U.S. Provisional Patent Application No. 62/787,860, filed on Jan. 3, 2019. These applications are hereby incorporated by reference herein.

TECHNICAL FIELD

This application relates to contrast enhanced imaging. More specifically, this application relates to contrast enhanced ultrasound for vascular imaging.

BACKGROUND

In contrast-enhanced imaging, a contrast agent is provided to an area or volume to be imaged in order to provide a higher signal strength from the area or volume, or selectively enhance signals from areas or volumes with high contrast concentration. For example, in contrast-enhanced ultrasound (CEUS), microbubbles may be injected into a subject's bloodstream and ultrasound images may be acquired of the subject's vasculature. Without the microbubbles, little to no signal may be provided by the blood vessels. In contrast accumulation imaging (CAI), multiple contrast-enhanced images (e.g., multiple image frames) are acquired and combined and/or normalized to form the final image, which can be used to map contrast agent progression and enhance vessel topology and conspicuity. Temporal accumulation imaging of CEUS has been commercialized and widely used for vascularity visualization. However, CEUS has limited spatial resolution due to the large size of the point spread function (PSF) in contrast mode. The PSF is a measure of blurring or spreading of a point source by an imaging system. CEUS may also have strong residual clutter artifacts as well as vulnerability to patient induced motion due to the combining of multiple image frames to form the final image.

FIG. 7 shows example (a) CEUS and (b) CAI images of a two-branch flow phantom with circulating microbubbles. As can be seen in FIG. 7(a), the CEUS image has "holes" in the visualization of the vasculature because microbubbles are not present at every point in the vasculature during a single image acquisition. A more complete image of the vasculature can be seen in the CAI image of FIG. 7(b). However, the CAI image suffers from low spatial resolution. In principle, CAI has similar spatial resolution to CEUS, however, in practice, its resolution is worse due to tissue motion and clutter artifacts. The clutter artifacts act as false positives for microbubbles and/or vasculature. For example, in the CAI image, there is visible residual clutter appearing as a haze at the left and right boundaries of the image as indicated by arrows 100 and 102, respectively. Furthermore, in both the CEUS image and the CAI image, line-shaped residual clutter is present as indicated by white arrows 104 and 106, which acts as a false positive for a vessel branch. Accordingly, improved contrast-enhanced accumulated imaging techniques with higher spatial resolution and reduced artifacts are desired.

SUMMARY

Systems and methods for performing imaging techniques with adjustable resolution and acquisition times, which may be tailored to different clinical applications intended for the visualization of different vascular levels of organs or diseases. The present disclosure describes a contrast accumulation imaging technique that may provide improved imaging performance that strategically selects multiple pixels to represent one or more microbubbles localized within an image. The systems and methods described herein may particularly localize each microbubble with its more specific characteristics and may provide better spatial resolution than CAI, adjustable spatial resolution, and/or less residual clutter than CAI which may result in higher contrast-to-tissue ratio (CTR). The system and methods described herein may provide contrast enhanced images at regular CEUS frame rates (e.g. 15-25 Hz) with shorter data acquisition times (e.g., approximately 20 s) compared to Super-resolution imaging.

In accordance with at least one example disclosed herein, an ultrasound imaging system may include an ultrasound probe for receiving ultrasound signals for a plurality of transmit/receive events, and at least one processor in communication with the ultrasound probe, the at least one processor configured to identify microbubbles in the ultrasound signals for the plurality of transmit/receive events, represent individual ones of the identified microbubbles as a plurality of pixels, wherein the plurality of pixels for individual ones of the identified microbubbles is less than a point spread function of the ultrasound imaging system, and combine the ultrasound signals including the represented microbubbles for the plurality of transmit/receive events to form an enhanced contrast accumulation image.

In accordance with at least one example disclosed herein, a method may include receiving a plurality of ultrasound images, identifying microbubbles in individual ones of the plurality of ultrasound images, representing the identified microbubbles as a plurality of pixels wherein the plurality of pixels of individual ones of the identified microbubbles is less than a point spread function, and combining at least two of the individual ones of the plurality of ultrasound images to provide an enhanced contrast accumulation image.

DESCRIPTION

Figure 1:
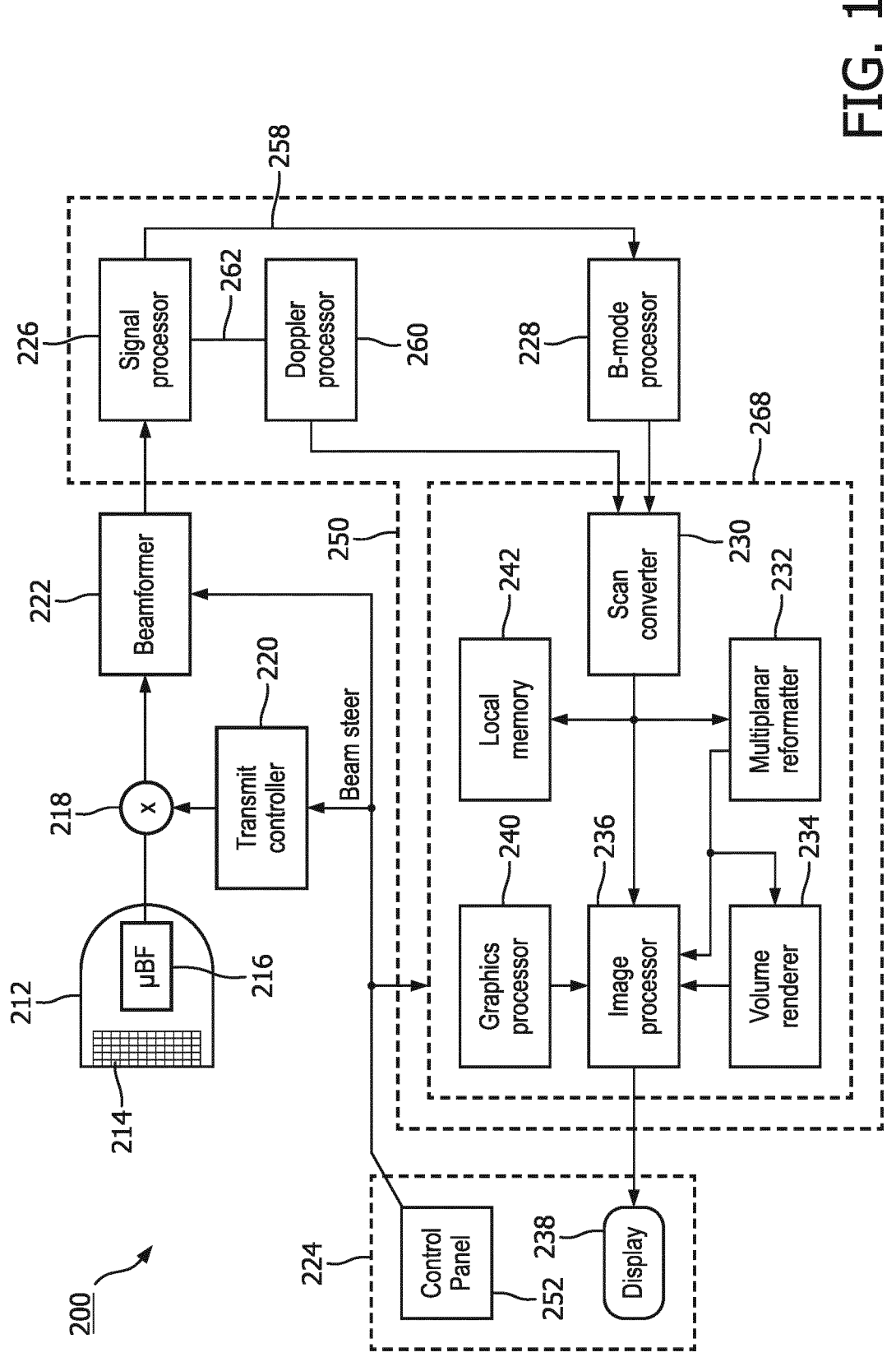
FIG. 1 is a block diagram of an ultrasound imaging system arranged in accordance with some examples of the present disclosure.

The following description of certain exemplary examples is merely exemplary in nature and is in no way intended to limit the invention or its applications or uses. In the following detailed description of examples of the present systems and methods, reference is made to the accompanying drawings which form a part hereof, and in which are shown by way of illustration specific examples in which the described systems and methods may be practiced. These examples are described in sufficient detail to enable those skilled in the art to practice the presently disclosed systems and methods, and it is to be understood that other examples may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Super-resolution imaging (SRI), also known as ultrasound localization microscopy (ULM), is another imaging technique for vasculature imaging and quantification. It has several advantages: (1) high spatial resolution (up to ~8 $\mu$m×10 $\mu$m, almost close to the size of red blood cells); (2) same penetration depth as regular CEUS; (3) quantification of blood flow in both magnitude and direction (also, optionally, speed of propagation); (4) non-invasive with non-toxic microbubble-based contrast agents; (5) no hardware modifications to existing clinical scanners. In a common SRI technique, each super-resolved image is obtained by two steps: (1) localizing the center of each separable microbubble and then (2) accumulating these centers over thousands of acquisitions. The position of each microbubble is obtained by taking the local maxima of each microbubble intensity profile. This means that the center of each microbubble can be seen and represented as a single-pixel dot. During localization, the center of each microbubble can be obtained also with the following methods: (1) directly finding the peak (maximum intensity) of each separable microbubble in image domain; or (2) fitting the microbubble image with a 2D/3D Gaussian function and then finding the peak; or (3) fitting the microbubble image with the PSF of the imaging system and then finding the peak. The term, "maximum pixel projection technique" is used to refer to the accumulation of center positions from multiple acquisitions (e.g., multiple image frames). The accumulation of the center positions of microbubbles is the probability density mapping of microbubbles, which is the super-resolved image of the microvasculature.

SRI typically requires tens or hundreds of thousands of individual contrast imaging frames, corresponding to a combination of very high imaging frame rates (often >500 Hz) and very long acquisition times (e.g., several minutes) compared to conventional contrast ultrasound scans. It is very challenging to achieve acceptable super-resolved images with regular CEUS frame rate (e.g., 15-25 Hz) and short acquisition time (e.g., 20 s). High imaging frame rate in SRI is preferable for (1) good separation of individual microbubbles, (2) sufficient accumulation of microbubbles, and (3) adequate motion compensation. SRI with low frame rate (~25 Hz, as in conventional CEUS) is limited by motion artifacts and requires prolonged acquisition times (>30 min). If the acquisition time is not sufficient, the super-resolved image may not be properly formed due to partial filling and a large number of "holes". Hemodynamically, large blood vessels (diameter>100 $\mu$m) get perfused more quickly. Hence, the acquisition time required to reconstruct them may be much shorter than for very small vessels (~20 $\mu$m and smaller). Since SRI is a technique developed to mainly image small structures—for example, capillaries with diameter less than 20 $\mu$m—the data acquisition time has to be long enough to reconstruct such microvessels.

Spatial resolution and temporal resolution of SRI may be related to the local concentration of microbubbles, given that this techniques reconstructs microvessels based on the localized sources (e.g., microbubbles) within them (e.g., single-pixel dot is used to represent each microbubble for accumulation). For example, a high concentration of microbubbles and an accumulation of 75,000 images (e.g., acquisition time of 150 s at frame rate of 500 Hz), yielding 1,000,000 events (e.g., microbubbles) may be used to generate one super-resolved image with 10 $\mu$m spatial resolution.

The present disclosure is directed to systems and methods for performing imaging techniques with adjustable resolution and acquisition times, which may be tailored to different clinical applications intended for the visualization of different vascular levels of organs or diseases. The present disclosure describes a contrast accumulation imaging technique that strategically selects multiple pixels to represent one or more microbubbles localized within an image, as opposed to a large number of pixels associated with a general PSF of CAI or a single pixel representation of SRI. The pixels representing microbubbles may be selected by applying a filter to the image data such that multiple pixels are representative of the microbubbles within the image data. In some examples, the filter may include an intensity threshold of a value between a maximum pixel intensity and a minimum pixel intensity associated with identified microbubbles. In other examples, the filter may select a certain percentage of pixels whose intensity is greater than the mean signal intensity. In yet other examples, the filter may include other thresholds or algorithms to select the pixels representative of the microbubbles. The pixel intensity values for the filter may be preset or estimated based on existing image data. This filtered technique may allow microbubbles of different intensity values to be localized and accumulated in subsequent imaging frames to achieve a high resolution image (e.g., an enhanced CAI image). The techniques described herein may be referred to as "enhanced CAI."

When a contrast agent, such as microbubbles, are present in the subject, contrast-enhanced images may be generated from the ultrasound signals. In some examples, the ultrasound imaging system may separate the signals to generate contrast images to visualize the contrast agent and tissue images to visualize tissue structures. In some examples, the ultrasound imaging system may include at least one processor configured to identify microbubbles in the ultrasound signals and/or the images. After identification, the at least one processor may localize the microbubbles by representing each identified microbubble by multiple pixels by passing the identified microbubbles through a filter. The number of pixels may depend on a threshold value of a filter. Multiple ultrasound signals (e.g., signals based on echoes received from multiple transmit/receive events) and/or multiple image frames processed by the at least one processor may be combined to form a final enhanced contrast accumulation image. In some examples, the at least one processor may perform motion estimation and compensation prior to accumulating the images. Optionally, in some examples, the at least one processor may pass the ultrasound signals and/or images through one or more clutter rejection filters.

FIG. 1 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as an intravascular ultrasound (IVUS) catheter probe. In other examples, the transducer array 214 may be in the form of a flexible array configured to be conformally applied to a surface of subject to be imaged (e.g., patient). The transducer array 214 is configured to transmit ultrasound signals (e.g., beams, waves) and receive echoes (e.g., received ultrasound signals) responsive to the transmitted ultrasound signals. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some examples, the transducer array 214 may be coupled to a microbeamformer 216, which may be located in the ultrasound probe 212, and which may control the transmission and reception of signals by the transducer elements in the array 214. In some examples, the microbeamformer 216 may control the transmission and reception of signals by active elements in the array 214 (e.g., an active subset of elements of the array that define the active aperture at any given time).

In some examples, the microbeamformer 216 may be coupled, e.g., by a probe cable or wirelessly, to a transmit/receive (T/R) switch 218, which switches between transmission and reception and protects the main beamformer 222 from high energy transmit signals. In some examples, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 214 under control of the microbeamformer 216 is directed by the transmit controller 220, which may be coupled to the T/R switch 218 and a main beamformer 222. The transmit controller 220 may control the direction in which beams are steered. Beams may be steered straight ahead from (orthogonal to) the transducer array 214, or at different angles for a wider field of view. The transmit controller 220 may also be coupled to a user interface 224 and receive input from the user's operation of a user control. The user interface 224 may include one or more input devices such as a control panel 252, which may include one or more mechanical controls (e.g., buttons, encoders, etc.), touch sensitive controls (e.g., a trackpad, a touchscreen, or the like), and/or other known input devices.

In some examples, the partially beamformed signals produced by the microbeamformer 216 may be coupled to a main beamformer 222 where partially beamformed signals from individual patches of transducer elements may be combined into a fully beamformed signal. In some examples, microbeamformer 216 is omitted, and the transducer array 214 is under the control of the beamformer 222 and beamformer 222 performs all beamforming of signals. In examples with and without the microbeamformer 216, the beamformed signals of beamformer 222 are coupled to processing circuitry 250, which may include one or more processors (e.g., a signal processor 226, a B-mode processor 228, a Doppler processor 260, and one or more image generation and processing components 268) configured to produce an ultrasound image from the beamformed signals (i.e., beamformed RF data).

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and electronic noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 258 which couples the signals from the signal processor 226 to a B-mode processor 228 for producing B-mode image data.

In some examples according to principles of the present disclosure, the signal processor 226 may analyze the RF data and/or IQ signals to identify and localize microbubbles in the signals. The processed signals may be provided to the B-mode processor 228 and other processing circuitry (e.g., scan converter, 230, image processor 236) for accumulation and generation of an enhanced CAI image. In some examples, the signal processor 226 may accumulate the signals over multiple transmit/receive events to generate a combined signal to be further processed into an enhanced CAI image by the B-mode processor 228 and other processing circuitry.

The B-mode processor 228 can employ amplitude detection for the imaging of structures in the body. According to principles of the present disclosure, the B-mode processor 228 may generate signals for tissue images and/or contrast images. Because microbubbles may generate much higher intensity echoes than the surrounding tissue, signals from the microbubbles may be extracted from the B-mode signal for forming a separate contrast image. Similarly, the lower intensity tissue signals may be separated from the microbubble signals for generating a tissue image. The signals produced by the B-mode processor 228 may be coupled to a scan converter 230 and/or a multiplanar reformatter 232. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format. In another example of the present disclosure, the scan converter 230 may arrange the echo signals into side-by-side contrast enhanced and tissue images. As explained further below, in some examples, the image processor 236 performs microbubble identification, localization, and accumulation.

The multiplanar reformatter 232 can convert echoes which are received from points in a common plane in a volumetric region of the body into an ultrasonic image (e.g., a B-mode image) of that plane, for example as described in U.S. Pat. No. 6,443,896 (Detmer). The scan converter 230 and multiplanar reformatter 232 may be implemented as one or more processors in some examples.

A volume renderer 234 may generate an image (also referred to as a projection, render, or rendering) of the 3D dataset as viewed from a given reference point, e.g., as described in U.S. Pat. No. 6,530,885 (Entrekin et al.). The volume renderer 234 may be implemented as one or more processors in some examples. The volume renderer 234 may generate a render, such as a positive render or a negative render, by any known or future known technique such as surface rendering and maximum intensity rendering.

In some examples, the system may include a Doppler signal path 262 which couples the output from the signal processor 226 to a Doppler processor 260. The Doppler processor 260 may be configured to estimate the Doppler shift and generate Doppler image data. The Doppler image data may include color data which is then overlaid with B-mode (i.e. grayscale) image data for display. The Doppler processor 260 may be configured to filter out unwanted signals (i.e., noise or clutter associated with non-moving tissue), for example using a wall filter. The Doppler processor 260 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo further threshold detection to further reduce noise, as well as segmentation and post-processing such as filling and smoothing. The velocity and power estimates may then be mapped to a desired range of display colors in accordance with a color map. The color data, also referred to as Doppler image data, may then be coupled to the scan converter 230, where the Doppler image data may be converted to the desired image format and overlaid on the B-mode image of the tissue structure to form a color Doppler or a power Doppler image. For example, Doppler image data may be overlaid on a B-mode image of the tissue structure.

Output (e.g., B-mode images, Doppler images) from the scan converter 230, the multiplanar reformatter 232, and/or the volume renderer 334 may be coupled to an image processor 236 for further enhancement, buffering and temporary storage before being displayed on an image display 238.

According to principles of the present disclosure, in some examples, the image processor 236 may analyze one or more images to identify and localize one or more microbubbles within an image based on multiple pixels per microbubble. In some examples, identifying microbubbles may include identifying a general microbubble region (e.g. using PSF) and then applying one or more filters to the general microbubble region to identify one or more particular microbubbles. In some examples, pixels with intensities greater than a threshold of the filter are classified as a microbubble. The one or more filters may further be used to localize the microbubbles by representing centers of the microbubbles as multiple pixels. The filters may be preset (e.g., based on exam type and/or contrast agent type) or based on the range of intensities presented in the microbubble region of the image. In other examples, the filters may be set by a user input. In some examples, the filters may apply threshold values and/or other selection algorithms for determining which pixels to visualize. In some examples, the threshold value may be an intensity value. Thus, in some examples, the threshold value is an intensity threshold which is less than the maximum intensity (e.g., 80%, 90%) and greater than the minimum intensity (e.g., 50%, 60%) of the microbubble so that the microbubble representation is a multi-pixel spot which is greater than one pixel but the extent of the pixels is less than the entire microbubble (e.g. PSF). As the percentage of the maximum intensity increases, the number of pixels representing each microbubble decreases and the resolution increases. By using this technique a plurality of microbubbles may be localized within the PSF, and each microbubble may have its own intensity or pixel signature in some examples. After localization, the image processor 236 may accumulate the localized microbubbles over multiple image frames and/or transmit/receive events.

Optionally the image processor 236 may apply clutter rejection filters to the one or more images prior to identifying and localizing the microbubbles. The image processor 236 may alternatively or additionally optionally apply other pre-processing steps prior to identifying and localizing the microbubbles including smoothing, detail enhancement, and/or additional noise suppression.

A graphics processor 240 may generate graphic overlays for display with the images. These graphic overlays can contain, e.g., standard identifying information such as patient name, date and time of the image, imaging parameters, and the like. For these purposes the graphics processor may be configured to receive input from the user interface 224, such as a typed patient name or other annotations. The user interface 244 can also be coupled to the multiplanar reformatter 232 for selection and control of a display of multiple multiplanar reformatted (MPR) images.

The system 200 may include local memory 242. Local memory 242 may be implemented as any suitable non-transitory computer readable medium (e.g., flash drive, disk drive). Local memory 242 may store data generated by the system 200 including B-mode images, masks, executable instructions, inputs provided by a user via the user interface 224, or any other information necessary for the operation of the system 200.

As mentioned previously system 200 includes user interface 224. User interface 224 may include display 238 and control panel 252. The display 238 may include a display device implemented using a variety of known display technologies, such as LCD, LED, OLED, or plasma display technology. In some examples, display 238 may comprise multiple displays. The control panel 252 may be configured to receive user inputs (e.g., exam type, filter values for microbubble localization). The control panel 252 may include one or more hard controls (e.g., buttons, knobs, dials, encoders, mouse, trackball or others). In some examples, the control panel 252 may additionally or alternatively include soft controls (e.g., GUI control elements or simply, GUI controls) provided on a touch sensitive display. In some examples, display 238 may be a touch sensitive display that includes one or more soft controls of the control panel 252.

According to principles of the present disclosure, in some examples, a user may set a threshold value of the filter for localizing the microbubbles via the user interface 224. As described above, adjusting the threshold value may adjust the resolution of the contrast accumulation image. Thus, by setting the threshold value, the user may have control over the resolution and/or required acquisition time. In some examples, the user may select a desired resolution and/or acquisition time and the imaging system 200 may calculate the corresponding threshold value for the filter. In some examples, the threshold value may be pre-set based on exam type, contrast agent type, and/or properties of the image (e.g., dynamic range).

Figure 2:
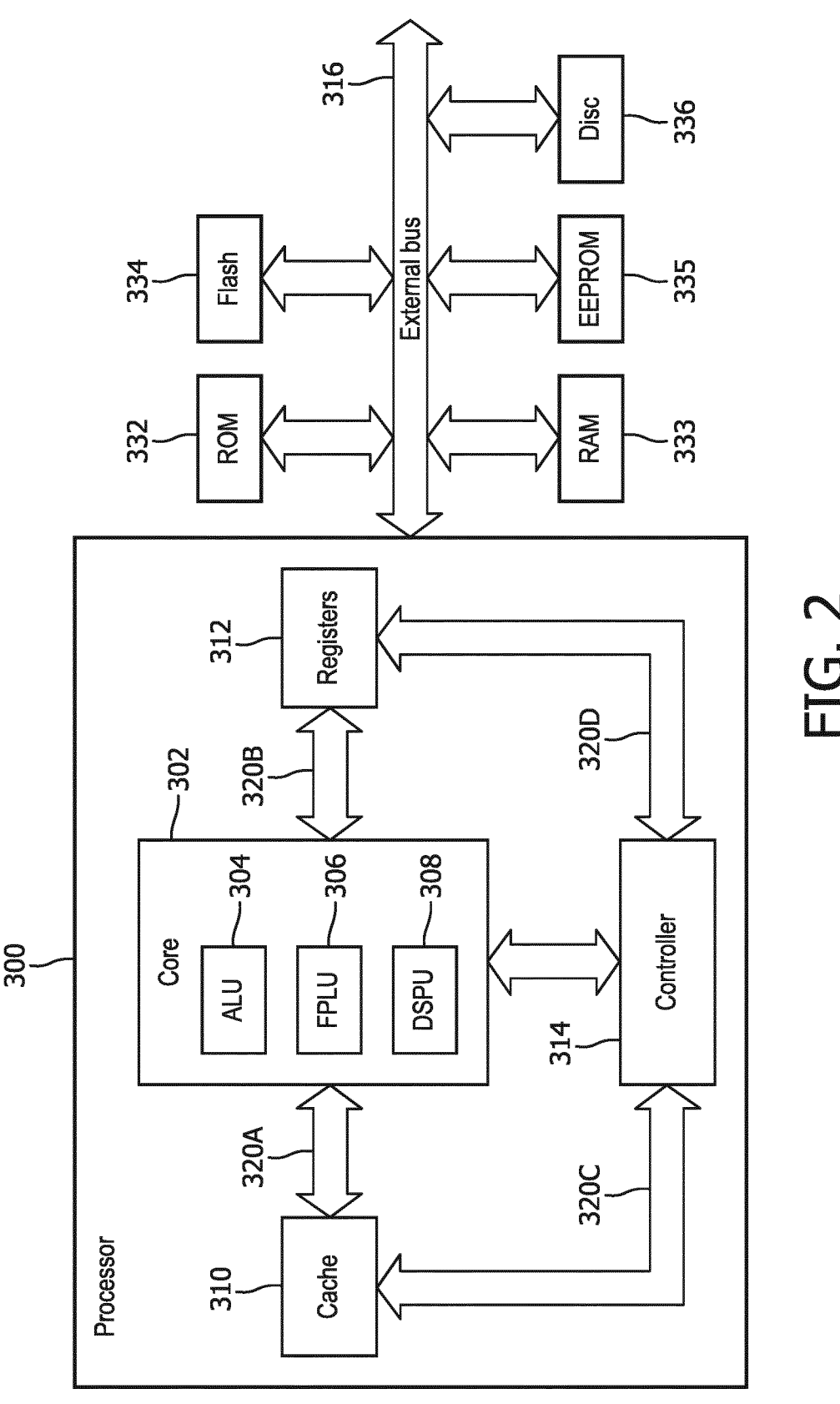
FIG. 2 is a block diagram illustrating an example processor in accordance with some examples of the present disclosure.

In some examples, various components shown in FIG. 2 may be combined. For instance, image processor 236 and graphics processor 240 may be implemented as a single processor. In another example, the scan converter 230 and multiplanar reformatter 232 may be implemented as a single processor. In some examples, various components shown in FIG. 2 may be implemented as separate components. For example, signal processor 226 may be implemented as separate signal processors for each imaging mode (e.g., B-mode, Doppler). In some examples, one or more of the various processors shown in FIG. 2 may be implemented by general purpose processors and/or microprocessors configured to perform the specified tasks. In some examples, one or more of the various processors may be implemented as application specific circuits. In some examples, one or more of the various processors (e.g., image processor 236) may be implemented with one or more graphical processing units (GPU).

FIG. 2 is a block diagram illustrating an example processor 300 according to principles of the present disclosure. Processor 300 may be used to implement one or more processors described herein, for example, image processor 236 shown in FIG. 1. Processor 300 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 300 may include one or more cores 302. The core 302 may include one or more arithmetic logic units (ALU) 804. In some examples, the core 302 may include a floating point logic unit (FPLU) 306 and/or a digital signal processing unit (DSPU) 308 in addition to or instead of the ALU 304.

The processor 300 may include one or more registers 312 communicatively coupled to the core 302. The registers 312 may be implemented using dedicated logic gate circuits (e.g., flip-flops) and/or any memory technology. In some examples the registers 312 may be implemented using static memory. The register may provide data, instructions and addresses to the core 302.

In some examples, processor 300 may include one or more levels of cache memory 310 communicatively coupled to the core 302. The cache memory 310 may provide computer-readable instructions to the core 302 for execution. The cache memory 810 may provide data for processing by the core 302. In some examples, the computer-readable instructions may have been provided to the cache memory 310 by a local memory, for example, local memory attached to the external bus 316. The cache memory 310 may be implemented with any suitable cache memory type, for example, metal-oxide semiconductor (MOS) memory such as static random access memory (SRAM), dynamic random access memory (DRAM), and/or any other suitable memory technology.

The processor 300 may include a controller 314, which may control input to the processor 300 from other processors and/or components included in a system (e.g., control panel 252 and scan converter 230 shown in FIG. 1) and/or outputs from the processor 300 to other processors and/or components included in the system (e.g., display 238 and volume renderer 234 shown in FIG. 1). Controller 314 may control the data paths in the ALU 304, FPLU 306 and/or DSPU 308. Controller 314 may be implemented as one or more state machines, data paths and/or dedicated control logic. The gates of controller 314 may be implemented as standalone gates, FPGA, ASIC or any other suitable technology.

The registers 312 and the cache 310 may communicate with controller 314 and core 302 via internal connections 320A, 320B, 320C and 320D. Internal connections may implemented as a bus, multiplexor, crossbar switch, and/or any other suitable connection technology.

Inputs and outputs for the processor 300 may be provided via a bus 316, which may include one or more conductive lines. The bus 316 may be communicatively coupled to one or more components of processor 300, for example the controller 314, cache 310, and/or register 312. The bus 316 may be coupled to one or more components of the system, such as display 238 and control panel 252 mentioned previously.

The bus 316 may be coupled to one or more external memories. The external memories may include Read Only Memory (ROM) 332. ROM 332 may be a masked ROM, Electronically Programmable Read Only Memory (EPROM) or any other suitable technology. The external memory may include Random Access Memory (RAM) 333. RAM 333 may be a static RAM, battery backed up static RAM, Dynamic RAM (DRAM) or any other suitable technology. The external memory may include Electrically Erasable Programmable Read Only Memory (EEPROM) 335. The external memory may include Flash memory 334. The external memory may include a magnetic storage device such as disc 336. In some examples, the external memories may be included in a system, such as ultrasound imaging system 200 shown in FIG. 2, for example local memory 242.

Figure 3:
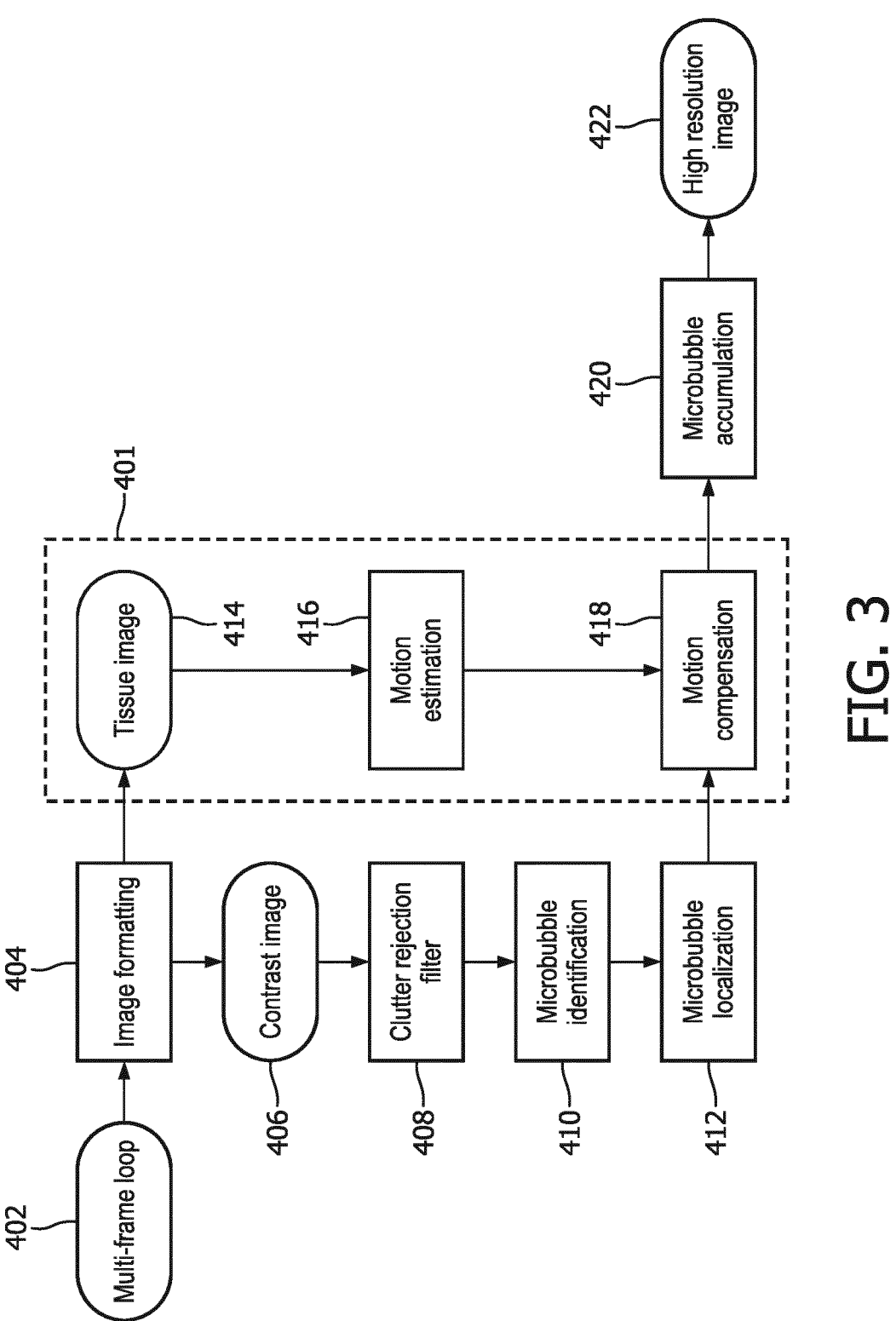
FIG. 3 is a flow chart of a method in accordance with some examples of the present disclosure.
Figure 4:
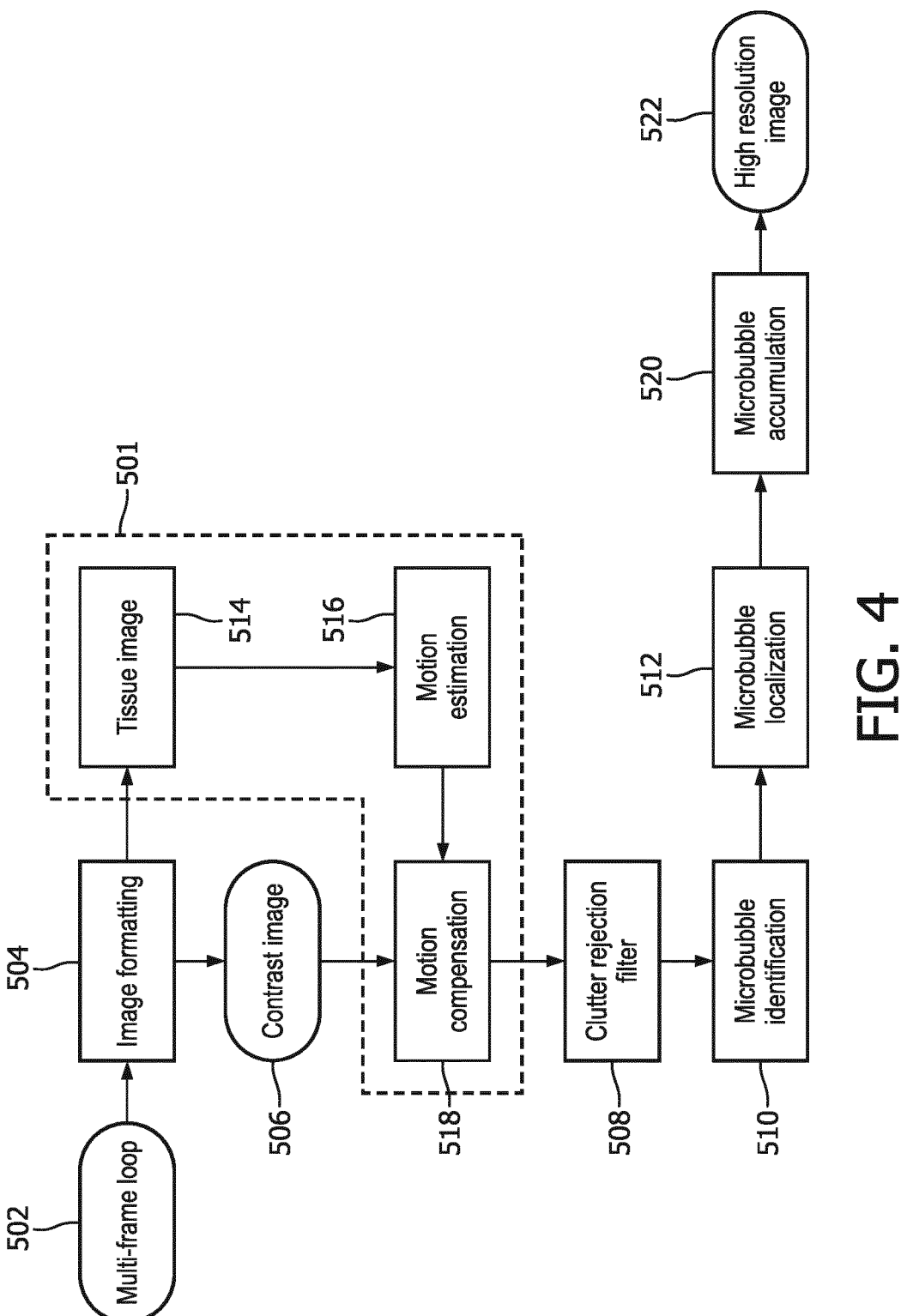
FIG. 4 is a flow chart of a method in accordance with some examples of the present disclosure.

FIGS. 3 and 4 are flow charts 400, 500 that illustrate steps of methods performed by an image processor, such as image processor 236 shown in FIG. 1, to perform methods in accordance with examples of the present disclosure. The steps in both flow charts 400, 500 are the same, but may be performed in different orders as will be described in detail below.

In some examples, a multi-frame loop (formats can be DICOM, AVI, WMV, JPEG, etc.) of conventional side-by-side contrast and tissue images may be used as inputs to the signal processor as indicated by blocks 402 and 502. The image-domain-based processing may be implemented as an off-line processing feature in some examples. In some applications, the images may be log-compressed with a limited dynamic range, thus, the image-domain implementation of enhanced CAI may have limited performance. In some examples, enhanced CAI may also be implemented at IQ-domain (input is IQ data) or RF-domain (input is RF data) rather than a multi-frame loop as shown in FIGS. 3 and 4. In some applications, IQ data and/or RF data may provide better performance of microbubble localization and clutter rejection. In examples using IQ and/or RF data, the image processor may receive data from a signal processor and/or beamformer, such as signal processor 226 and/or beamformer 222 shown in FIG. 1. Alternatively, in these examples, the steps shown in FIGS. 3 and 4 may be performed by the signal processor.

At blocks 404 and 504, the image processor may perform image formatting. In some examples, the multi-frame loops are processed to separate the tissue and contrast images so that they can be processed independently as indicated by blocks 406 and 506 and blocks 414 and 514. The tissue and contrast images may be properly formatted for following processing blocks. For example, red-green-blue (RGB) images may be converted to gray-scale images (or indexed images) with a desired dynamic range (e.g., normalized from 0 to 1). In examples where enhanced CAI is performed on RF data and/or IQ data rather than a multi-frame loop, image formatting may include separating signals resultant from the contrast agent and signals resultant from the tissue.

Optionally, at blocks 408 and 508, clutter rejection filtering may be performed on contrast images prior to temporal accumulation, which may reduce the effect of stationary echoes (especially in the near field), reverbs, etc. Clutter rejection filters can be implemented as finite impulse response (FIR), infinite impulse response (IIR)-based high-pass filters with sufficient numbers of coefficient delay pairs (e.g., taps), a polynomial least-squares curve fitting filter, and/or singular value decomposition (SVD)-based high-pass filter. Filter parameters may be optimized to suppress most of the residual clutter but preserve most of the contrast signals. In some examples, blocks 408 and 508 may be omitted.

At blocks 410 and 510, microbubble identification may be performed. Separable individual microbubbles may be identified in this step. An optional interpolation step can be performed to bring the image pixel size to a desired resolution (e.g. 50 μm×50 μm) in some examples. Next, an intensity-based thresholding may be performed to remove background noise. For example, normalized intensities less than the threshold (e.g. 35% of maximum intensity) may be considered background noise and set to zero. Additionally, a local maxima search may be performed to find the locations of microbubbles. In some examples, to make sure the identified microbubbles are separable and not clustered, only one microbubble may be identified (e.g., the one with the maximum intensity) within any PSF area (e.g., microbubble region). In some examples, microbubbles may be identified by methods similar to those described above with reference to generating SRI images.

At blocks 412 and 512, microbubble localization may be performed. Localization refers to generating the visual representation of each identified microbubble (e.g., multi-pixel spot), which may be established in this step. The identified microbubbles are passed through a filter that applies a threshold value or other algorithm for selecting which pixels of the microbubbles to visualize. In the example of a filter including a threshold value, only pixels of the microbubble above the threshold value may be visualized. A threshold (e.g. 70%, 80%, 90% of maximum intensity of the microbubble) may be pre-defined based on different imaging settings or exam-type based presets. Typically, the threshold is less than 100% and greater than 50% of the maximum intensity of the microbubble. This threshold can be used to adjust the spatial resolution. For a higher spatial resolution (e.g., fewer pixels), a longer acquisition time may be used. For a lower spatial resolution (e.g., more pixels), a shorter acquisition time may be used. Within the microbubble region (e.g., the PSF), if the intensity ratio (e.g., normalized to maximum intensity) is greater than or equal to the threshold, the pixels may be defined as the representation of the microbubble. In other examples, the filter may include other algorithms or operators for selecting pixels for visualization. For example, the filter may select a certain percentage of pixels whose intensity is greater than a mean signal intensity of the microbubble, all microbubbles, or image.

In some examples, different intensity values may be assigned to different pixels of the microbubble representation (e.g., visualization). In some examples, the pixel intensities within the microbubble representation remain unchanged and the rest of the microbubble pixel intensities (e.g., the portions of the microbubbles not visualized) may be set to zero. Different algorithms for value assignment may be implemented in other examples. For example, all of the pixels of the microbubble above the threshold value may be set to a uniform intensity value in some examples. The uniform intensity may be based on an average intensity of the pixels above the threshold value or a maximum intensity of the pixels above the threshold value in some examples.

Motion compensation may be performed before microbubble accumulation. As shown by dashed boxes 401 and 501, motion compensation may be provided at different points in the process of enhanced CAI in various examples of the present disclosure. In some examples, the tissue images 414 and 514 may be used for motion compensation. That is, movement of tissue structures in the tissue images 414 and 514 may be used to estimate displacements due to motion. In some examples, the motion compensation on contrast images alone may be used. If there is not much motion in the multi-frame loop 402, contrast images may be used alone for enhanced CAI, bypassing the tissue image pathway in box 401 as shown in FIG. 3. However, in some applications, using only the contrast images may be less reliable.

In the example shown in FIG. 3, motion compensation is performed after microbubble localization. At block 416, estimated displacements from the tissue images 414 are performed. At block 418, the estimated displacements calculated at block 416 may be used to compensate for motion in the outputs of the microbubble localization step shown in block 412.

Alternatively, as shown in FIG. 4, motion compensation may be performed prior to microbubble identification. The dashed box 501 of FIG. 4 shows the estimated displacements from the tissue images 514 calculated at block 516 are used to compensate for motion on the contrast images at block 518 before microbubble localization is performed at block 510. The method shown in FIG. 4 may allow for motion compensated contrast images for display. However, the method shown in FIG. 3 may reduce the computational cost of motion compensation, but may come at the expense of not providing motion compensated contrast images for display.

After motion compensation, microbubble accumulation is performed at blocks 410 and 520. A high resolution image 422 and 522 is output from the accumulation step. In some examples, accumulation may be performed by summing multiple image frames from the multi-frame loop, for example, sequential image frames. In some examples, multiple frames may be summed followed by a normalization step. In some examples, multiple frames may be analyzed to determine the maximum pixel intensity for each location in the image may be determined and the maximum pixel intensity values may be used to generate the final image 522. In examples where microbubble identification and localization are performed by processing IQ and/or RF data, the processed ultrasound signals from multiple transmit/receive events may be summed or otherwise combined. The combined ultrasound signals may then be provided to other processing components (e.g., B-mode processor, scan converter) for generating a final image.

Figure 5:
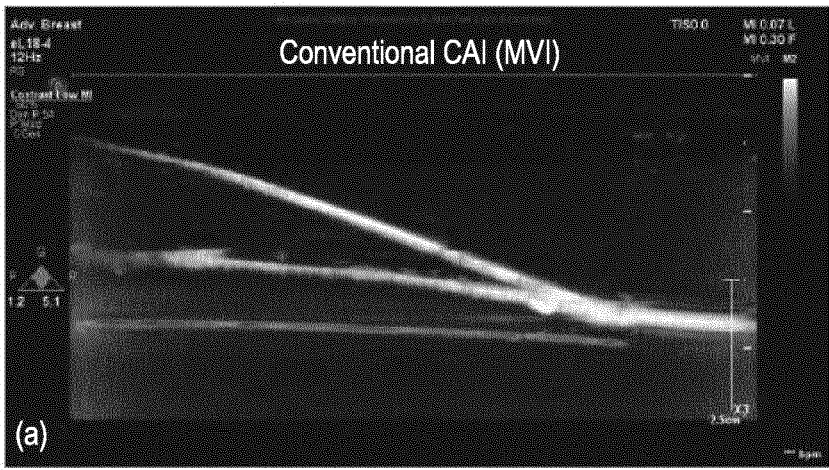
FIG. 5 shows example contrast enhanced images in a flow phantom in accordance with some examples of the present disclosure.
Figure 5:
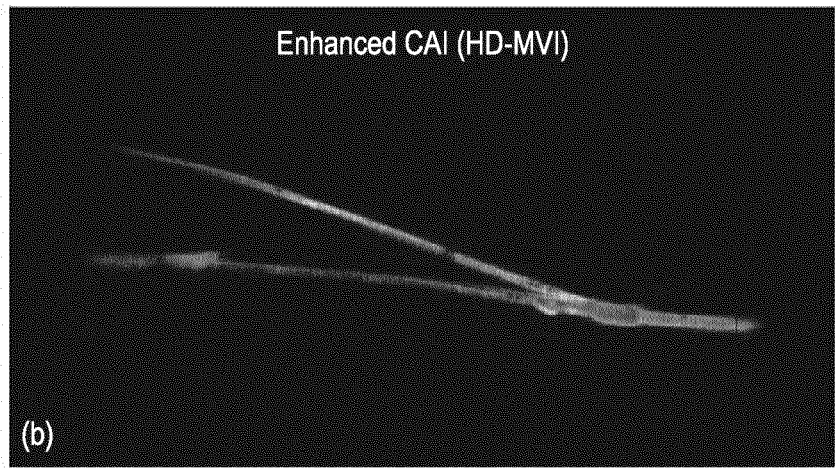
Figure 5:
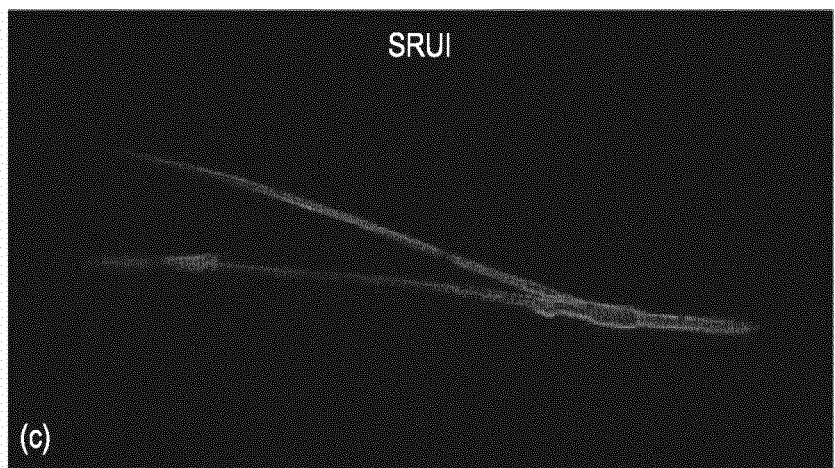

FIG. 5 shows example CAI, enhanced CAI, and SRI images of a flow phantom. The conventional CAI image is shown in pane (a). The enhanced CAI image in accordance with examples of the present disclosure is shown in pane (b), and the SRI is shown in pane (c). The data acquisition time was 180 s and the frame rate was 12 Hz. The enhanced CAI image in pane (b) shows better spatial resolution and better CTR compared to conventional CAI in pane (a). Additionally, due to insufficient number of localized microbubbles accumulated within the data acquisition time, SRI image shown in pane (c) has many "holes" in visualizing the phantom vessels and the phantom vessels are not completely filled.

Figure 6:
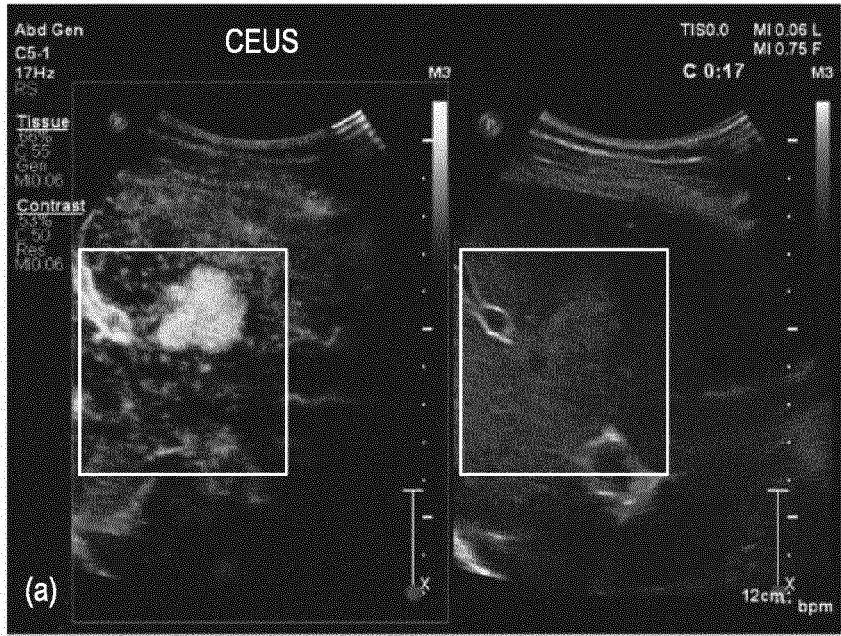
FIG. 6 shows example in vivo contrast enhanced images of a liver in accordance with some examples of the present disclosure.
Figure 6:
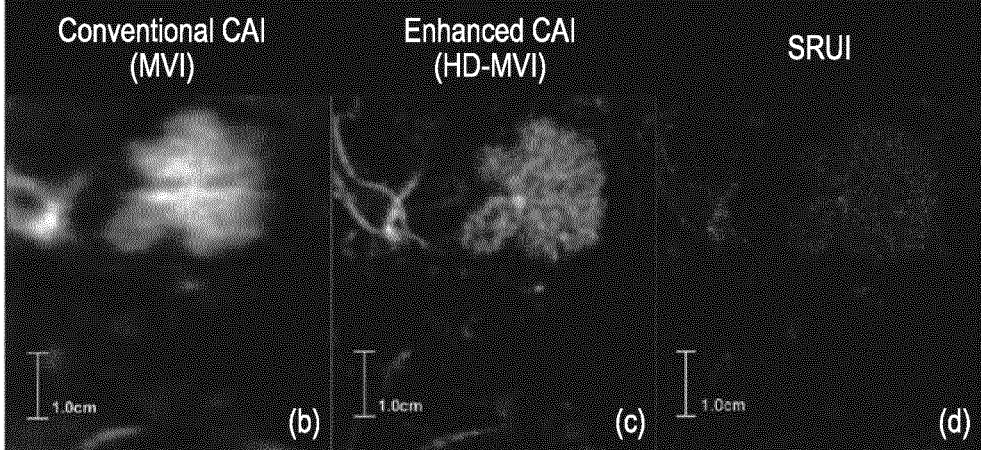
Figure 7:
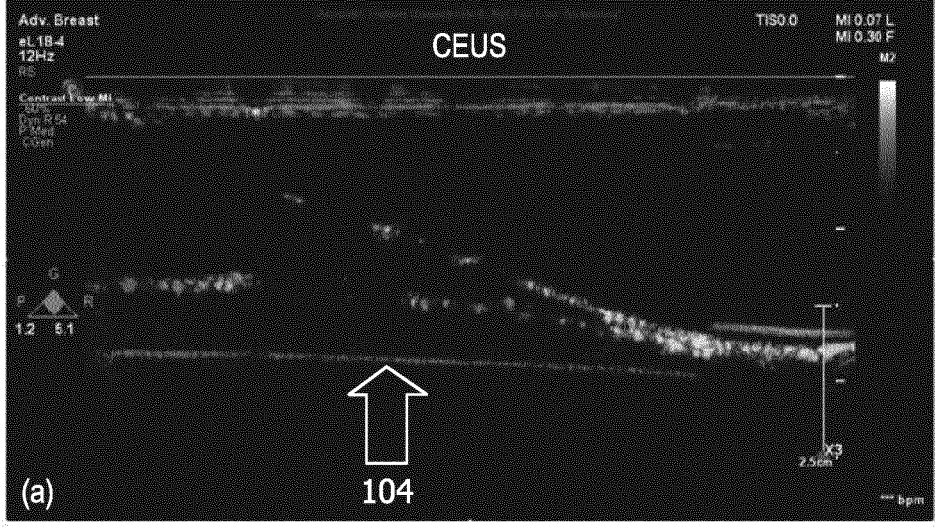
FIG. 7 shows example contrast enhanced images.
Figure 7:
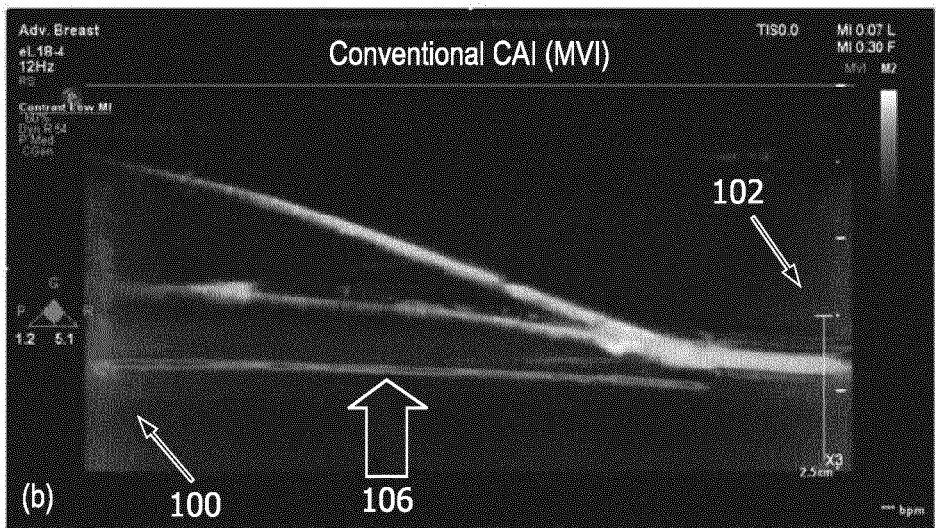

FIG. 6 shows example in vivo images of a human liver. Pane (a) shows side-by-side contrast (left side) and tissue images (right side). Pane (b) shows a conventional CAI image, pane (c) shows an enhanced CAI image in accordance with examples described herein, and pane (d) shows an SRI image. The data acquisition time was 17 s and the frame rate was 17 Hz. There was significant respiratory motion of the liver in this example. As seen in pane (c), enhanced CAI image shows better spatial resolution compared to conventional CAI shown in pane (b). Additionally, due to insufficient data acquisition time, SRI image shown in pane (d) is not properly formed due to bad filling with many "holes".

The examples provided in FIGS. 5 and 6 demonstrate the potential advantages of the proposed systems and methods described herein (e.g., enhanced CAI): better spatial resolution compared to conventional CAI, ability to use regular CEUS frame rates, and/or shorter data acquisition time relative to SRI. Furthermore, the systems and methods described herein allow uses to adjust the representation of the microbubbles (e.g., the number of pixels) to control the spatial resolution of the images. This may give users more control over the trade-offs between resolution and acquisition time.

In various examples where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, examples or processes described herein may be combined with one or more other examples, examples and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular example or group of examples. Thus, while the present system has been described in particular detail with reference to exemplary examples, it should also be appreciated that numerous modifications and alternative examples may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. An ultrasound imaging system comprising:
an ultrasound probe for receiving ultrasound signals for a plurality of transmit/receive events; and
at least one processor in communication with the ultrasound probe, the at least one processor configured to:
identify microbubbles in the ultrasound signals for the plurality of transmit/receive events;
represent individual ones of the identified microbubbles as a multi-pixel spot comprising a plurality of pixels, wherein the plurality of pixels for individual ones of the identified microbubbles is less than a number of pixels representative of the entire extent of the identified microbubble according to a point spread function of the ultrasound imaging system and greater than a single pixel;

combine the ultrasound signals including the represented microbubbles for the plurality of transmit/receive events to form an enhanced contrast accumulation image; and represent the individual ones of the identified microbubbles as the multi-pixel spot by passing the ultrasound signals of each identified microbubble through a filter that applies an intensity threshold for selecting which pixels of the identified microbubble to visualize, wherein the filter is based on a range of intensities presented in the identified microbubble, wherein the intensity threshold is less than a maximum intensity and greater than a minimum intensity of the identified microbubble, and wherein only pixels of the identified microbubble above the intensity threshold are represented in the individual ones of the plurality of ultrasound images; wherein the intensity threshold is set as a percentage of the maximum intensity of the identified microbubble, such that, as the percentage increases, the number of pixels of the identified microbubble that exceed the intensity threshold decreases.

2. The ultrasound system of claim 1, wherein a number of the plurality of pixels is based at least in part, on the filter applied to the ultrasound signals.

3. The ultrasound imaging system of claim 1, further comprising a user interface configured to receive a user input, wherein the user input includes the intensity threshold.

4. The ultrasound imaging system of claim 1, wherein the at least one processor is configured to form a plurality of ultrasound images corresponding to the ultrasound signals of the plurality of transmit/receive events, wherein the at least one processor is configured to identify microbubbles in the ultrasound signals after the ultrasound signals have been used to form the plurality of ultrasound images.

5. The ultrasound imaging system of claim 4, wherein the at least one processor is configured to analyze the plurality of ultrasound images to separate ultrasound signals resulting from tissue structures and ultrasound signals resulting from the microbubbles prior to identifying microbubbles.

6. The ultrasound imaging system of claim 1, wherein the filter is a clutter rejection filter that includes at least one of a finite impulse response high-pass filter, an infinite impulse response high-pass filter, a polynomial least-squares curve fitting filter, or a singular value decomposition high-pass filter.

7. The ultrasound imaging system of claim 1, wherein the at least one processor is configured to perform motion compensation.

8. The ultrasound imaging system of claim 7, wherein the motion compensation is performed on the represented microbubbles.

9. The ultrasound imaging system of claim 7, wherein the at least one processor is configured to form a plurality of ultrasound images corresponding to the ultrasound signals of the plurality of transmit/receive events, and wherein the motion estimation and compensation is performed on the plurality of ultrasound images.

10. A method comprising:

receiving a plurality of ultrasound images;

identifying microbubbles in individual ones of the plurality of ultrasound images;

representing the identified microbubbles as a multi-pixel spot comprising a plurality of pixels wherein the plurality of pixels of individual ones of the identified microbubbles is less than a number of pixels representative of the entire extent of the identified microbubble according to a point spread function and greater than a single pixel; and combining at least two of the individual ones of the plurality of ultrasound images to provide an enhanced contrast accumulation image, and wherein:

representing comprises passing each identified microbubble through a filter that applies an intensity threshold for selecting which pixels of the microbubble to visualize, wherein the filter is based on a range of intensities presented in the identified microbubble, wherein the intensity threshold is less than a maximum intensity and greater than a minimum intensity of the identified microbubble, and wherein only pixels of the identified microbubble above the intensity threshold are represented in the individual ones of the plurality of ultrasound images; wherein the intensity threshold is set as a percentage of the maximum intensity of the identified microbubble, such that, as the percentage increases, the number of pixels of the identified microbubble that exceed the intensity threshold decreases.

11. The method of claim 10, further comprising setting the intensity threshold based on a user input.

12. The method of claim 10, wherein identifying the microbubbles comprises performing a local maxima search on individual ones of the plurality of ultrasound images.

13. The method of claim 12, wherein only one local maxima may be found within a region defined by the point spread function.

14. The method of claim 10, further comprising:

estimating displacements due to motion after representing the identified microbubbles; and adjusting locations of the represented microbubbles based on the estimated displacements.

15. The method of claim 10, further comprising:

estimating displacements due to motion prior to identifying the microbubbles in the individual ones of the plurality of ultrasound images; and adjusting the individual ones of the plurality of ultrasound images based on the estimated displacements.

16. The method of claim 15, wherein motion of tissue structures in the individual ones of the plurality of ultrasound images are used to estimate the displacements.

17. The method of claim 10, further comprising formatting the plurality of ultrasound images to separate tissue images of the plurality of ultrasound images from contrast images of the plurality of ultrasound images, wherein the individual ones of the plurality of ultrasound images correspond to the contrast images.

\* \* \* \* \*